United States Patent
Loiseleur et al.

(10) Patent No.: US 10,952,435 B2
(45) Date of Patent: Mar. 23, 2021

(54) PYRIDINE-2-CARBOXAMIDES AS NEMATOCIDES

(71) Applicant: SYNGENTA PARTICIPATIONS AG, Basel (CH)

(72) Inventors: Olivier Loiseleur, Stein (CH); Andre Jeanguenat, Stein (CH); Regis Jean Georges Mondiere, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 486 days.

(21) Appl. No.: 14/905,548

(22) PCT Filed: Jul. 11, 2014

(86) PCT No.: PCT/EP2014/064890
§ 371 (c)(1),
(2) Date: Jan. 15, 2016

(87) PCT Pub. No.: WO2015/007626
PCT Pub. Date: Jan. 22, 2015

(65) Prior Publication Data
US 2016/0165887 A1  Jun. 16, 2016

(30) Foreign Application Priority Data

Jul. 18, 2013 (EP) ................... 13177127

(51) Int. Cl.
*A01N 43/40* (2006.01)
*C07D 213/81* (2006.01)

(52) U.S. Cl.
CPC ........... *A01N 43/40* (2013.01); *C07D 213/81* (2013.01)

(58) Field of Classification Search
None
See application file for complete search history.

(56) References Cited

U.S. PATENT DOCUMENTS

| 2010/0022389 A1* | 1/2010 | Langewald | A01N 43/56 504/100 |
| 2011/0136831 A1* | 6/2011 | Oda | A01N 37/18 514/255.06 |
| 2014/0323736 A1* | 10/2014 | Schwarz | A61K 31/166 546/316 |

FOREIGN PATENT DOCUMENTS

| WO | 2013064461 A2 | 5/2013 | |
| WO | 2013076230 A1 | 5/2013 | |
| WO | WO 2013076230 A1 * | 5/2013 | ........... A61K 31/166 |

OTHER PUBLICATIONS

STN registry database compound 1092-35-9 (entered STN Nov. 16, 1984).*
Jasmer et al. (Annu. Rev. Phytopathol., 2003, 41, 245-70) (Year: 2003).*
International Search Report & Written Opinion for PCT/EP2014/064890, dated Sep. 19, 2014.

* cited by examiner

*Primary Examiner* — Jared Barsky
(74) *Attorney, Agent, or Firm* — Baker & Hostetler LLP; Toni-Junell Herbert

(57) ABSTRACT

Compounds of the formula (I), in which the substituents are as defined in claim 1, are suitable for use as nematicides.

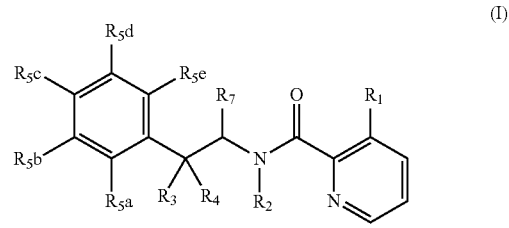

19 Claims, No Drawings

PYRIDINE-2-CARBOXAMIDES AS NEMATOCIDES

RELATED APPLICATION INFORMATION

This application is a 371 of International Application No. PCT/EP2014/064890, filed Jul. 11, 2014, which claims priority to European Patent Application No. 13177127.1, filed Jul. 8, 2013, the contents of all of which are incorporated herein by reference herein.

The present invention relates to novel carboxamide compounds, a process for the preparation of these compounds and their use as pesticides, in particular nematicides.

Carboxamides are described, for example, in WO2005/058828, WO2013/076230, WO2013/064461, WO2013/064460.

Novel phenethyl amides containing a 3-substituted pyrid-2-yl moiety have now been found, which show good pesticidal, in particular nematicidal, activity.

The present invention thus relates to a method of protecting crops of useful plants against damages caused by nematode pests, which comprises treating the plants or the locus thereof with a compound of the formula (I)

wherein

R1 represents halogen, cyano, C1-C2-alkyl, C1-C2-haloalkyl, C1-C2-alkoxy, C1-C2-haloalkoxy or C1-C2-haloalkylthio;

R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl, C3-C6-cycloalkoxyor benzyl;

R3 and R4 independently of each other represent hydrogen and fluorine;

R5a, R5b, R5c, R5d and R5e independently of each other represent hydrogen, halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

each R6 independently of each other represents halogen, C1-C4-alkyl or C1-C4-haloalkyl;

R7 represents hydrogen or methyl;

as well as agronomically acceptable salts, enantiomers, diastereomers, tautomers and N-oxides of these compounds.

In the substituent definitions of the compounds of the formula I, each alkyl moiety either alone or as part of a larger group (such as alkoxy, alkylthio, alkoxycarbonyl and alkylcarbonyl) is a straight or branched chain and is, for example, methyl, ethyl, n-propyl, n-butyl, isopropyl, sec-butyl, isobutyl or tert-butyl.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. Preferably, the alkenyl and alkynyl moieties contain 2 to 4 carbon atoms.

Halogen is fluorine, chlorine, bromine or iodine, preferably fluorine, chlorine or bromine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

The following list provides definitions, including preferred definitions, for substituents R1, R2, R3, R4, R5a, R5b, R5c, R5d, R5e, R6 and R7 with reference to compounds of formula (I). For any one of these substituents, any of the definitions given below may be combined with any definition of any other substituent given below or elsewhere in this document.

R1 represents halogen, cyano, C1-C2-alkyl, C1-C2-haloalkyl, C1-C2-alkoxy, C1-C2-haloalkoxy or C1-C2-haloalkylthio.

Preferably, R1 represents halogen, cyano, C1-C2-alkyl or C1-C2-haloalkyl.

More preferably, R1 represents halogen, cyano, methyl or trifluromethyl.

Even more preferably, R1 represents halogen, methyl or trifluoromethyl.

R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl, C3-C6-cycloalkoxy or benzyl.

Most preferably, R2 represents hydrogen.

R3 and R4 independently of each other represent hydrogen or fluorine.

R3 and R4 preferably are each hydrogen

R5a, R5b, R5c, R5d and R5e independently of each other represent hydrogen, halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6.

Preferably, R5a, R5b, R5c, R5d and R5e independently of each other represent hydrogen, halogen, cyano, C1-C4-alkyl, C1-C4-haloalkyl, C1-C4-alkoxy, C1-C4-haloalkoxy, C3-C6-cycloalkyl, C2-C6-alkenyl or C2-C6-haloalkynyl, wherein cycloalkyl is optionally substituted by one or more substituents R6 and alkenyl is substituted by one or more R6.

More preferably, R5a, R5b, R5c, R5d and R5e independently of each other represent hydrogen, halogen, cyano, C1-C2-alkyl, C1-C2-haloalkyl, C1-C2-alkoxy, C1-C2-haloalkoxy, C3-C4-cycloalkyl, C2-C4-alkenyl or C2-C4 haloalkynyl, wherein cycloalkyl is optionally substituted by one or more substituents R6 and C2-C4-alkenyl is substituted by one or more R6.

Even more preferably, R5a, R5b, R5c, R5d and R5e independently of each other represent hydrogen, halogen, cyano, C1-C2-haloalkyl or C1-C2-haloalkoxy.

More preferably again, R5a, R5b, R5c, R5d and R5e independently of each other represent hydrogen, fluoro, chloro, bromo, cyano, difluoromethyl, trifluoromethyl, difluoromethoxy or trifluoromethoxy.

Yet more preferably, R5a represents hydrogen, fluoro, chloro, bromo, methyl or methoxy;

R5b represents hydrogen, fluoro or chloro;

R5c represents hydrogen, fluoro, chloro, bromo, cyano, methoxy, difluoromethyl, trifluoromethyl, difluoromethoxy or trifluoromethoxy;

R5e represents hydrogen, fluoro, chloro or trifluoromethyl.

Most preferably, R5e represents fluoro.

Preferably, at least two of R5a, R5b, R5c, R5d and R5e represent hydrogen.

More preferably, at least three of R5a, R5b, R5c, R5d and R5e represent hydrogen.

Most preferably, R5a, R5b and R5d represent hydrogen.

Each R6 independently of each other represents halogen, C1-C4-alkyl or C1-C4-haloalkyl.

Each R6 independently of each other represents halogen, or C1-C2-haloalkyl.

R7 represents hydrogen or methyl.

Preferably, R7 represents hydrogen.

In another group of compounds, R7 preferably represents methyl.

In one group of compounds,

R1 represents halogen, cyano, C1-C2-alkyl or C1-C2-haloalkyl;

R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl C3-C6-cycloalkoxy or benzyl;

R3 and R4 independently of each other represent hydrogen or fluorine;

R5a, R5b, R5c, R5d and R5e independently of each other represent hydrogen, halogen, cyano, C1-C4-alkyl, C1-C4-haloalkyl, C1-C4-alkoxy, C1-C4-haloalkoxy, C3-C6-cycloalkyl, C2-C6-alkenyl or C2-C6 haloalkynyl, wherein cycloalkyl is optionally substituted by one or more substituents R6 and alkenyl is substituted by one or more R6;

each R6 independently of each other represents halogen, C1-C4-alkyl or C1-C4-haloalkyl;

R7 is hydrogen.

In another group of compounds,

R1 represents halogen, cyano, C1-C2-alkyl or C1-C2-haloalkyl;

R2 represents hydrogen, C1-C4-alkyl, C1-C4-alkoxy, C1-C4-alkoxycarbonyl, cyanomethyl, C2-C4-alkenyl, C2-C4-alkynyl, C3-C6-cycloalkylcarbonyl, C3-C6-cycloalkoxy or benzyl;

R3 and R4 independently of each other represent hydrogen or fluorine;

R5a, R5b, R5c, R5d and R5e independently of each other represent hydrogen, halogen, cyano, C1-C4-alkyl, C1-C4-haloalkyl, C1-C4-alkoxy, C1-C4-haloalkoxy, C3-C6-cycloalkyl, C2-C6-alkenyl or C2-C6 haloalkynyl, wherein cycloalkyl is optionally substituted by one or more substituents R6 and C2-C6-alkenyl is substituted by one or more R6;

each R6 independently of each other represents halogen, C1-C4-alkyl, C1-C4-haloalkyl;

R7 represents hydrogen.

In another group of compounds, R3 and R4 each represent fluorine.

In another group of compounds, R3 represents hydrogen and R4 represents fluorine.

In another group of compounds, R3 and R4 each represent hydrogen.

In another group of compounds,

R1 represents halogen, cyano, methyl or trifluromethyl;

R2 represents hydrogen;

R3 and R4 independently of each other represent hydrogen or fluorine;

R5a, R5b, R5c, R5d and R5e independently of each other represent hydrogen, halogen, cyano, C1-C4-haloalkyl or C1-C4-haloalkoxy;

R7 is hydrogen.

In another group of compounds,

R1 represents halogen, methyl or trifluoromethyl;

R2 represents hydrogen;

R3 and R4 independently of each other represent hydrogen or fluorine;

R5a, R5b, R5c, R5d and R5e independently of each other represent hydrogen, fluoro, chloro, bromo, cyano, difluoromethyl, trifluoromethyl, difluoromethoxy or trifluoromethoxy;

R7 is hydrogen.

In another group of compounds, R1 represents halogen, methyl or trifluoromethyl;

R2 represents hydrogen;

R3 and R4 independently of each other represent hydrogen or fluorine;

R5c represents fluoro, chloro, bromo, cyano, difluoromethyl, trifluoromethyl, difluoromethoxy or trifluoromethoxy;

R5e represents fluoro;

R7 is hydrogen.

In another group of compounds, R1 represents halogen, methyl or trifluoromethyl;

R2 represents hydrogen;

R3 and R4 independently of each other represent hydrogen or fluorine;

R5a represents hydrogen, fluoro, chloro, bromo, methyl or methoxy;

R5b represents hydrogen, fluoro or chloro;

R5c represents hydrogen, fluoro, chloro, bromo, cyano, methoxy, difluoromethyl, trifluoromethyl, difluoromethoxy or trifluoromethoxy;

R5e represents hydrogen, fluoro, chloro or trifluoromethyl;

R7 is hydrogen.

Some of the compounds of formula (I) are novel. Accordingly, the invention also provides compounds of the formula (I) wherein R1, R2, R3, R4, R5a, R5b, R5c, R5d, R5e, R6 and R7 are as described, as well as agronomically acceptable salts, enantiomers, diastereomers, tautomers and N-oxides of these compounds, provided that the compound of formula (I) is not:

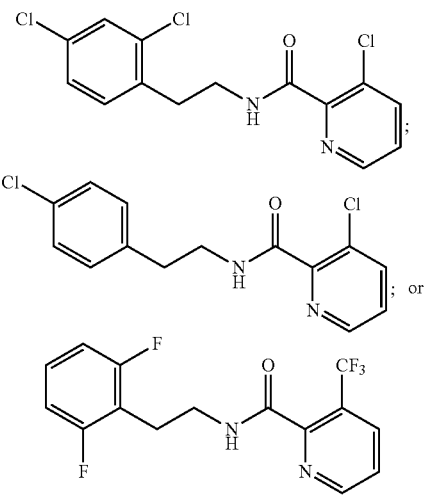

The preferred definitions of R1, R2, R3, R4, R5a, R5b, R5c, R5d, R5e, R6 and R7 described above likewise apply to this group of novel compounds of formula (I).

In one group of novel compounds of formula (I), R1 represents halogen, cyano, C1-C2-alkyl, C1-C2-haloalkyl, C1-C2-alkoxy, C1-C2-haloalkoxy or C1-C2-haloalkylthio;

R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl, C3-C6-cycloalkoxy or benzyl;

R3 and R4 independently of each other represent hydrogen and fluorine;

R5a, R5b and R5d independently of each other represent hydrogen, halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5c represents halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5e represents fluoro;

each R6 independently of each other represents halogen, C1-C4-alkyl or C1-C4-haloalkyl;

R7 represents hydrogen or methyl;

as well as agronomically acceptable salts, enantiomers, diastereomers, tautomers and N-oxides of these compounds.

Preferably in this group of compounds, R5c represents halogen, cyano, C1-C4-alkyl, C1-C4-haloalkyl, C1-C4-alkoxy, C1-C4-haloalkoxy, C3-C6-cycloalkyl, C2-C6-alkenyl or C2-C6 haloalkynyl, wherein cycloalkyl is optionally substituted by one or more substituents R6 and alkenyl is substituted by one or more R6.

More preferably in this group of compounds, R5c represents halogen, cyano, C1-C4-haloalkyl or C1-C4-haloalkoxy.

Most preferably in this group of compounds, R5c represents fluoro, chloro, bromo, cyano, difluoromethyl, trifluoromethyl, difluoromethoxy or trifluoromethoxy.

The preferred definitions of R1, R2, R3, R4, R5a, R5b, R5d, R6 and R7 described above likewise apply to this group of novel compounds of formula (I).

In another group of novel compounds of formula (I), R1 represents halogen, cyano, C1-C2-alkyl, C1-C2-haloalkyl, C1-C2-alkoxy, C1-C2-haloalkoxy or C1-C2-haloalkylthio;

R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl, C3-C6-cycloalkoxy or benzyl;

R3 and R4 independently of each other represent hydrogen and fluorine;

R5a, R5b and R5d independently of each other represent hydrogen, halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5c represents hydrogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5e represents chloro;

each R6 independently of each other represents halogen, C1-C4-alkyl or C1-C4-haloalkyl;

R7 represents hydrogen or methyl;

as well as agronomically acceptable salts, enantiomers, diastereomers, tautomers and N-oxides of these compounds.

Preferably in this group of compounds, R5c represents hydrogen, cyano, C1-C4-alkyl, C1-C4-haloalkyl, C1-C4-alkoxy, C1-C4-haloalkoxy, C3-C6-cycloalkyl, C2-C6-alkenyl or C2-C6 haloalkynyl, wherein cycloalkyl is optionally substituted by one or more substituents R6 and alkenyl is substituted by one or more R6.

More preferably in this group of compounds, R5c represents hydrogen, cyano, C1-C4-haloalkyl or C1-C4-haloalkoxy.

Most preferably in this group of compounds, R5c represents hydrogen, cyano, difluoromethyl, trifluoromethyl, difluoromethoxy or trifluoromethoxy.

The preferred definitions of R1, R2, R3, R4, R5a, R5b, R5d, R6 and R7 described above likewise apply to this group of novel compounds of formula (I).

Certain intermediates that can be used to prepare compounds of formula (I) are novel and as such also form part of the invention, such as particular compounds of formula (II).

Accordingly, in a further aspect, the invention provides the compounds of formula (II)

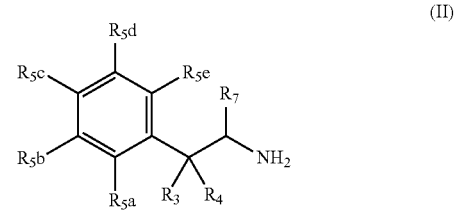

wherein R3, R4, R5a, R5b, R5c, R5d, R5e and R7 are as herein for compounds of formula (I). The preferred definitions of R3, R4, R5a, R5b, R5c, R5d, R5e and R7 defined in respect of compounds of formula (I) also apply to compounds of formula (II).

Compounds of formula (Ib), that is a compound of formula (I) wherein R2 is hydrogen can be prepared from amines of the formula (II) wherein R2 is hydrogen and R3, R4, R5a, R5b, R5c, R5d, R5e and R7 are as defined herein for compounds of formula (I), and acylating agents of the formula (III), wherein Xb is halogen, hydroxy or $C_{1-6}$ alkoxy, preferably chloro, and R1 is as defined herein for compounds of formula (I), in the presence of a base, such as triethylamine, Hünig base, sodium bicarbonate, sodium carbonate, potassium carbonate, pyridine or quinoline, but preferably triethylamine, and generally in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C. When Xb is hydroxyl, a coupling agent, such as benzotriazol-1-yloxytris(dimethylamino) phosphoniumhexafluorophosphate, bis-(2-oxo-3-oxazolidi-nyl)-phosphinic acid chloride (BOP—Cl), N,N'-dicyclohexylcarbodiimide (DCC) or 1,1'-carbonyl-diimidazole (CDI), may be used, as described in L. A. Paquette, Encyclopaedia of Reagents for Organic Synthesis, Vol 3. Wiley, England, 1995 pp 1751-1754. Acylating agents of the formula (III) are known or are easily prepared by those skilled in the art.

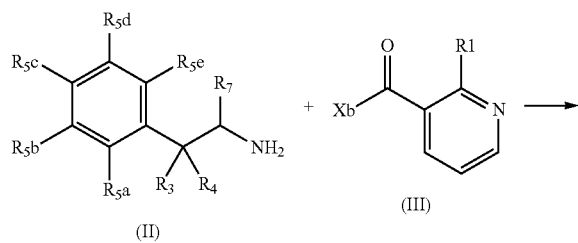

Amines of the formula (IIa), that is an amine of formula (II) wherein R7 is hydrogen, can be prepared by treating nitriles of the formula (IV), wherein R3, R4, R5a, R5b, R5c, R5d and R5e are as defined herein for a compound of formula (I), with a reducing agent. A typical reducing agent is hydrogen. Typically such a hydrogenation would be facilitated by a catalyst. Typical catalysts are metals, metal salts, or metal complexes. Examples of such type of catalytic hydrogenations are listed in in R. C. Larock Comprehensive Organic Transformations, Wiley-VCH, 1999, pp 875-876. Other typical reducing agents are hydrides. Typical hydrides are borohydrides, or aluminium hydrides, examples of which are sodium borohydride or lithium aluminium hydride. Such hydride reductions can be facilitated by the use of other components such as metal salts. Other typical reducing agents are boranes. Typical boranes are borane-tetrahydrofurane or -dimethylsulfide complexes. Examples of such type of reductions are listed in in R. C. Larock Comprehensive Organic Transformations, Wiley-VCH, 1999, pp 875-876.

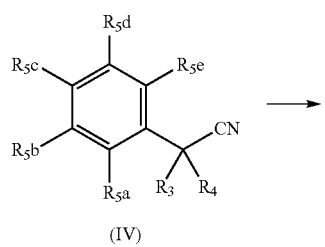

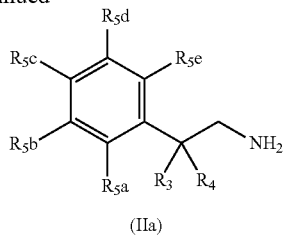

Nitriles of formula (IV) in which R3 and R4 are hydrogen are known or can be prepared according to various methods reported in the literature. An example is given in F. Stazi et al, Synthesis 2010, 19, 3332-3338.

Compounds of formula (I) in which R2 is as defined under formula I but is not hydrogen can be prepared from compounds of formula (Ib), that is a compound of formula (I) wherein R2 is hydrogen, and a reagent of the formula (VI), wherein R2 is as defined herein for a compound of formula (I) and Xc is a leaving group, such as halide, mesylate, tosylate or triflate. This reaction is conveniently done in the presence of a base. Typical reagents of formula (VI) and the appropriate base are described in P. J. Kocienski, Protecting groups, Thieme, Germany, 2000 and T. W. Green, P. G. M. Wuts, Protective groups in organic synthesis, Wiley, USA, 1999 or are known by those skilled in the art.

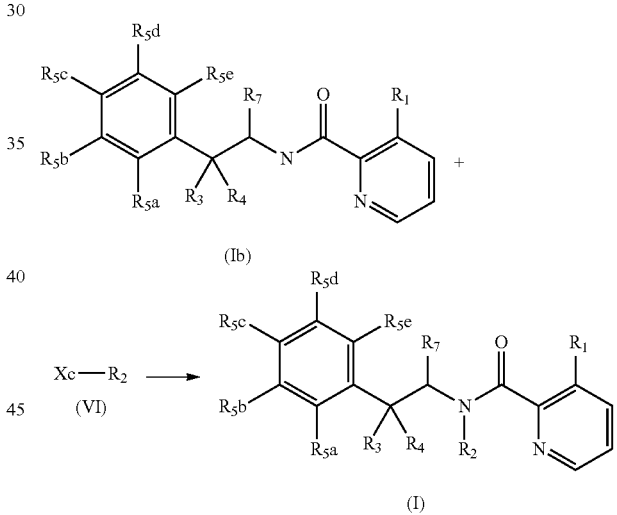

For preparing all further compounds of the formula (I) functionalized according to the definitions of R1, R2, R3, R4, R5, R7 and R8, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

These reactions can be conveniently performed in a solvent.

These reactions can be conveniently performed at various temperatures.

These reactions can be conveniently performed in an inert atmosphere.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent. A salt is chosen depending on its tolerances for compound's use, such as agricultural or physiological tolerance.

Salts of compounds of formula (I) can be converted in the customary manner into the free compounds (I), acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615 or C. White, Science, vol 318, p. 783, 2007.

It can be advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

Tables 1 to 11: Compounds of Formula (IA)

The invention is further illustrated by making available the following individual compounds of formula (IA) listed below in Tables 1 to 11.

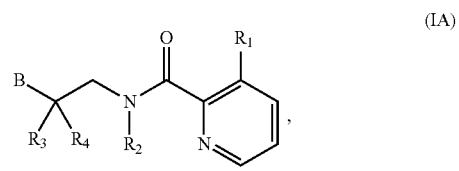

Each of Tables 1 to 11, which follow the Table Y below, make available 89 compounds of the formula (IA) in which $R_1$, $R_2$, $R_3$ and $R_4$ are the substituents defined in Table Y and B is the substituent defined in the relevant Table 1 to 11. Thus Table 1 individualises 89 compounds of formula (IA) wherein for each row of Table Y, the B substituent is as defined in Table 1; similarly, Table 2 individualises 89 compounds of formula (IA) wherein for each row of Table Y, the B substituent is as defined in Table 2; and so on for Tables 3 to 11.

TABLE Y

| Compound No. | $R_1$ | $R_2$ | $R_3$ | $R_4$ |
|---|---|---|---|---|
| Y.001 | CF3 | H | H | H |
| Y.002 | CF3 | CH3 | H | H |
| Y.003 | CF3 | C(=O)—CH3 | H | H |
| Y.004 | CF3 | OC(=O)—CH3 | H | H |
| Y.005 | CF3 | allyl | H | H |
| Y.006 | CF3 | propargyl | H | H |
| Y.007 | CF3 | H | F | H |
| Y.008 | CF3 | CH3 | F | H |
| Y.009 | CF3 | C(=O)—CH3 | F | H |
| Y.010 | CF3 | OC(=O)—CH3 | F | H |
| Y.011 | CF3 | allyl | F | H |
| Y.012 | CF3 | propargyl | F | H |
| Y.013 | CF3 | H | F | F |
| Y.014 | CF3 | CH3 | F | F |
| Y.015 | CF3 | C(=O)—CH3 | F | F |
| Y.016 | CF3 | OC(=O)—CH3 | F | F |
| Y.017 | CF3 | allyl | F | F |
| Y.018 | CF3 | propargyl | F | F |
| Y.019 | Cl | H | H | H |
| Y.020 | Cl | CH3 | H | H |
| Y.021 | Cl | C(=O)—CH3 | H | H |
| Y.022 | Cl | OC(=O)—CH3 | H | H |
| Y.023 | Cl | allyl | H | H |
| Y.024 | Cl | propargyl | H | H |
| Y.025 | Cl | H | F | H |
| Y.026 | Cl | CH3 | F | H |
| Y.027 | Cl | C(=O)—CH3 | F | H |
| Y.028 | Cl | OC(=O)—CH3 | F | H |
| Y.029 | Cl | allyl | F | H |
| Y.030 | Cl | propargyl | F | H |
| Y.031 | Cl | H | F | F |
| Y.032 | Cl | CH3 | F | F |
| Y.033 | Cl | C(=O)—CH3 | F | F |
| Y.034 | Cl | OC(=O)—CH3 | F | F |
| Y.035 | Cl | allyl | F | F |
| Y.036 | Cl | propargyl | F | F |
| Y.037 | Br | H | H | H |
| Y.038 | Br | CH3 | H | H |
| Y.039 | Br | C(=O)—CH3 | H | H |
| Y.040 | Br | OC(=O)—CH3 | H | H |
| Y.041 | Br | allyl | H | H |
| Y.042 | Br | propargyl | H | H |
| Y.043 | Br | H | F | H |
| Y.044 | Br | CH3 | F | H |
| Y.045 | Br | C(=O)—CH3 | F | H |
| Y.046 | Br | OC(=O)—CH3 | F | H |
| Y.047 | Br | allyl | F | H |
| Y.048 | Br | propargyl | F | H |
| Y.049 | Br | H | F | F |
| Y.050 | Br | CH3 | F | F |
| Y.051 | Br | C(=O)—CH3 | F | F |
| Y.052 | Br | OC(=O)—CH3 | F | F |
| Y.053 | Br | allyl | F | F |
| Y.054 | Br | propargyl | F | F |
| Y.055 | F | H | H | H |
| Y.056 | F | CH3 | H | H |
| Y.057 | F | C(=O)—CH3 | H | H |
| Y.058 | F | OC(=O)—CH3 | H | H |
| Y.059 | F | allyl | H | H |
| Y.060 | F | propargyl | H | H |
| Y.061 | F | H | F | H |
| Y.062 | F | CH3 | F | H |
| Y.063 | F | C(=O)—CH3 | F | H |
| Y.064 | F | OC(=O)—CH3 | F | H |
| Y.065 | F | allyl | F | H |
| Y.066 | F | propargyl | F | H |
| Y.067 | F | H | F | F |
| Y.068 | F | CH3 | F | F |
| Y.069 | F | C(=O)—CH3 | F | F |
| Y.070 | F | OC(=O)—CH3 | F | F |
| Y.071 | F | allyl | F | F |
| Y.072 | F | propargyl | F | F |
| Y.073 | CH3 | H | H | H |
| Y.074 | CH3 | CH3 | H | H |
| Y.075 | CH3 | C(=O)—CH3 | H | H |
| Y.076 | CH3 | OC(=O)—CH3 | H | H |
| Y.077 | CH3 | allyl | H | H |
| Y.078 | CH3 | propargyl | H | H |
| Y.079 | CH3 | H | F | H |
| Y.080 | CH3 | CH3 | F | H |
| Y.081 | CH3 | C(=O)—CH3 | F | H |
| Y.082 | CH3 | OC(=O)—CH3 | F | H |
| Y.083 | CH3 | allyl | F | H |
| Y.084 | CH3 | propargyl | F | H |
| Y.085 | CH3 | H | F | F |
| Y.086 | CH3 | CH3 | F | F |
| Y.087 | CH3 | C(=O)—CH3 | F | F |
| Y.088 | CH3 | OC(=O)—CH3 | F | F |
| Y.089 | CH3 | allyl | F | F |

Table 1 provides 89 compounds of formula (I), wherein B is

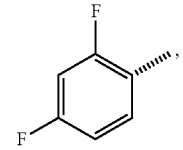

(2,4-difluorophenyl) wherein the broken line indicates the point of attachment of the group B to the compound of formula (IA), and R1, R2, R3 and R4 are as defined in each row of Table Y. For example, compound 1.001 has the following structure:

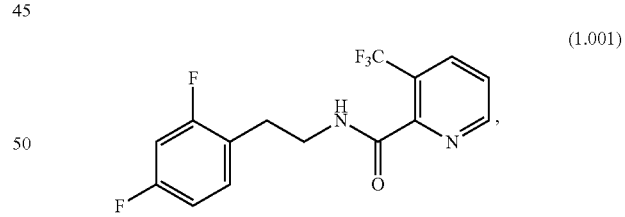

Table 2 provides 89 compounds of formula (IA) wherein B is 4-chloro-2-fluorophenyl (B2) and R1, R2, R3 and R4 are as defined in each row of Table Y.

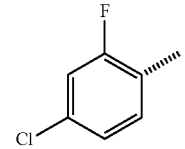

Table 3 provides 89 compounds of formula (IA) wherein B is 4-bromo-2-fluorophenyl (B3) and R1, R2, R3 and R4 are as defined in each row of Table Y.

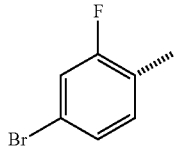
(B3)

Table 4 provides 89 compounds of formula (IA) wherein B is 4-cyano-2-fluorophenyl (B4) and R1, R2, R3 and R4 are as defined in each row of Table Y.

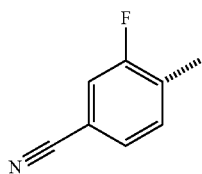
(B4)

Table 5 provides 89 compounds of formula (IA) wherein B is 4-trifluoromethyl-2-fluorophenyl (B5) and R1, R2, R3 and R4 are as defined in each row of Table Y.

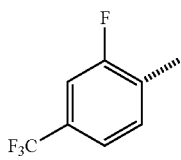
(B5)

Table 6 provides 89 compounds of formula (IA) wherein B is 4-trifluoromethoxy-2-fluorophenyl (B6) and R1, R2, R3 and R4 are as defined in each row of Table Y.

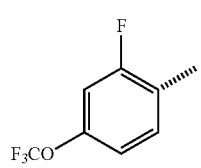
(B6)

Table 7 provides 89 compounds of formula (IA) wherein B is 4-diluoromethoxy-2-fluorophenyl (B7) and R1, R2, R3 and R4 are as defined in each row of Table Y.

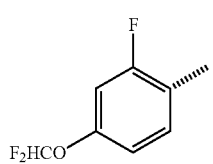
(B7)

Table 8 provides 89 compounds of formula (IA) wherein B is 4-cyclopropyl-2-fluorophenyl (B8) and R1, R2, R3 and R4 are as defined in each row of Table Y.

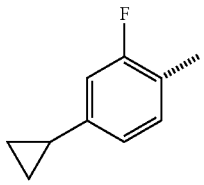
(B8)

Table 9 provides 89 compounds of formula (IA) wherein B is 4-(2-trifluoromethyl-cycloprop-1-yl)-2-fluorophenyl (B9) and R1, R2, R3 and R4 are as defined in each row of Table Y.

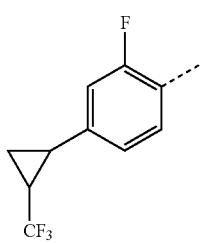
(B9)

Table 10 provides 89 compounds of formula (IA) wherein B is 4-methoxy-2-fluorophenyl (B10) and R1, R2, R3 and R4 are as defined in each row of Table Y.

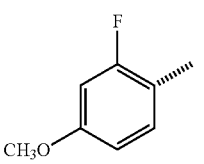
(B10)

Table 11 provides 89 compounds of formula (IA) wherein B is 2,4,6-trifluorophenyl (B11) and R1, R2, R3 and R4 are as defined in each row of Table Y.

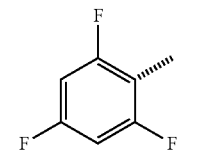
(B11)

The compounds according to the invention can be used for controlling or destroying pests such as insects and/or fungi which occur in particular on plants, especially on useful plants and ornamentals in agriculture, in horticulture and in forests, or on organs, such as fruits, flowers, foliage, stalks, tubers, seeds or roots, of such plants, and in some cases even plant organs which are formed at a later point in time remain protected against these pests. The compounds of formula (I) according to the invention are preventively and/or curatively valuable active ingredients in the field of pest control, even at low rates of application, which can be used against pesticide resistant pests such as insects and fungi, which compounds of formula (I) have a very favorable biocidal spectrum and are well tolerated by warm-blooded species, fish and plants. Accordingly, the present invention also makes available a pesticidal composition comprising compounds of the invention, such as formula (I).

It has now been found that the compounds of formula (I) according to the invention have, for practical purposes, a very advantageous spectrum of activities for protecting animals and useful plants against attack and damage by nematodes. Accordingly, the present invention also makes available a nematicidal composition comprising compounds of the invention, such as formula (I).

The compounds of formula (I) are especially useful for the control of nematodes. Thus, in a further aspect, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Helicotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; *false rootknot nematodes, Nacobbus* species; *Needle nematodes, Longidorus elongatus* and *other Longidorus* species; *Pin nematodes, Pratylenchus* species; *Lesion nematodes, Pratylenchus neglectus, Pratylenchus penetrans, Pratylenchus curvitatus, Pratylenchus goodeyi* and *other Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

Particularly, the nematode species *Meloidogyne* spp., *Heterodera* spp., *Rotylenchus* spp. and *Pratylenchus* spp. can be controlled by compounds of the invention.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulation auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematocides, plant activators, acaricides, and insecticides.

Accordingly, the present invention also makes available a composition comprising a compound of the invention and an agronomicaly carrier and optionally one or more customary formulation auxiliaries.

The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

Examples of compositions for use in agriculture are emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—a compound according to the invention and the type of composition is to be selected to suit the intended aims and the prevailing circumstances.

Examples of suitable liquid carriers are unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Examples of solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion. Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art. The compounds of the present invention are particularly suited for use in soil and seed treatment applications.

In general, the pre-mix compositions of the invention contain 0.5 to 99.9 especially 1 to 95, advantageously 1 to 50, %, by mass of the desired ingredients, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

A compound of the formula (I) in a preferred embodiment, independent of any other embodiments, is in the form of a plant propagation material treating (or protecting) composition, wherein said plant propagation material protecting composition may comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

Examples of application methods for the compounds of the invention and compositions thereof, that is the methods of controlling pests in the agriculture, are spraying, atomizing, dusting, brushing on, dressing, scattering or pouring—which are to be selected to suit the intended aims of the prevailing circumstances.

One method of application in agriculture is application to the foliage of the plants (foliar application), it being possible to select frequency and rate of application to match the danger of infestation with the pest/fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddy-field. The application of the compounds of the present invention to the soil is a preferred application method.

Typical rates of application per hectare is generally 1 to 2000 g of active ingredient per hectare, in particular 10 to 1000 g/ha, preferably 10 to 600 g/ha, such as 50 to 300 g/ha.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds. The application of the compounds of the present invention to seeds is a preferred application method.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula I, which is a preferred application method, can be carried out by any known methods, such as spraying or by dusting the seeds before sowing or during the sowing/planting of the seeds.

Suitable target plants are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous plants, such as beans, lentils, peas or soya; oil plants, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as flowers, amd lawn grass or turf).

In an embodiment, the plant is selected from cereals, corn, soybean, rice, sugarcane, vegetables and oil plants.

The term "plant" is to be understood as including also plants which have been so transformed by the use of recombinant DNA techniques that they are capable of synthesising one or more selectively acting toxins, such as are known, for example, from toxin-producing bacteria, especially those of the genus *Bacillus* and also plants which have been selected or hybridised to preserve and/or attain a desired trait, such as insect, fungi and/or nematode resistance.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic plants are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Compounds of this invention are effective for controlling nematode, insect, acarid pests and/or fungal pathogens of agronomic plants, both growing and harvested, when employed alone, they may also be used in combination with other biological active agents used in agriculture, such as one or more nematicides, insecticides, acaricides, fungicides, bactericides, plant activator, molluscicide, and pheromones (whether chemical or biological). Mixing the compounds of the invention or the compositions thereof in the use form as pesticides with other pesticides frequently results in a broader pesticidal spectrum of action. For example, the formula (I) compounds of this invention may be used effectively in conjunction or combination with pyrethroids, neonicotinoids, macrolides, diamides, phosphates, carbamates, cyclodienes, formamidines, phenol tin compounds, chlorinated hydrocarbons, benzoylphenyl ureas, pyrroles and the like.

The activity of the compositions according to the invention can be broadened considerably, and adapted to prevailing circumstances, by adding, for example, one or more insecticidally, acaricidally, nematicidally and/or fungicidally active agents. The combinations compounds of formula (I) with other insecticidally, acaricidally, nematicidally and/or fungicidally active agents may also have further surprising advantages which can also be described, in a wider sense, as synergistic activity. For example, better tolerance by plants, reduced phytotoxicity, pests or fungi can be controlled in their different development stages or better behaviour during their production, for example during grinding or mixing, during their storage or during their use.

The following list of pesticides together with which the compounds according to the invention can be used, is intended to illustrate the possible combinations by way of example.

The following combination of the compounds of formula (I) with another active compounds are preferred (the abbreviation "TX" means a compound of the formula I, preferably a compound selected from the compounds described in Tables 1 to 11 shown above and, more preferably, Table A shown below):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (995)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+

TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1395)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (495)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of Adoxophyes orana GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Pasteuria penetrans*+TX, *Pasteuria thornei*+TX, *Pasteuria nishizawae*+

TX, *Pasteuria ramosa*+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl) aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) [CCN]+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hyprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, 0-5-dichloro-4-iodophenyl O-ethyl ethylphosphonothioate (IUPAC name) (1057)+TX, 0,0-diethyl 0-4-methyl-2-oxo-2H-chromen-7-yl phosphorothioate (IUPAC name) (1074)+TX, 0,0-diethyl 0-6-methyl-2-propylpyrimidin-4-yl phosphorothioate (IUPAC name) (1075)+TX, 0,0,0',0'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesamolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-

30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, and 3-difluoromethyl-1-methyl-1H-pyrazole-4-carboxylic acid (3',4',5'-trifluoro-biphenyl-2-yl)-amide (dislosed in WO 2006/087343)+TX.

The references in square brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address: http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The mass ratio of of any two ingredients in each combination is selected as to give the desired, for example, synergistic action. In general, the mass ratio would vary depending on the specific ingredient and how many ingredients are present in the combination. Generally, the mass ratio between any two ingredients in any combination of the present invention, independently of one another, is from 100:1 to 1:100, including from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99. Preferred mass ratios between any two components of present invention are from 75:1 to 1:75, more preferably, 50:1 to 1.50, especially 25:1 to 1:25, advantageously 10:1 to 1:10, such as 5:1 to 1:5, for example 1:3 to 3:1. The mixing ratios are understood to include, on the one hand, ratios by mass and also, on other hand, molar ratios.

The combinations of the present invention (i.e. those comprising a compound of the present invention and one or more other biological active agents) may be applied simultaneously or sequentially.

In the event, the ingredients of a combination are applied sequentially (i.e., one after the other), the ingredients are applied sequentially within a reasonable period of each other to attain the biological performance, such as within a few hours or days. The order of applying the ingredients in the combination, i.e., whether the compounds of formula (I) should be applied first or not is not essential for working the present invention.

In the event ingredients of the combinations are applied simultaneously in the present invention, they may be applied as a composition containing the combination, in which case (A) the compound of formula (I) and the one or more other ingredients in the combinations can be obtained from separate formulation sources and mixed together (known as a tank-mix, ready-to-apply, spray broth, or slurry), or (B) the compound of formula (I) and the one or more other ingredients can be obtained as single formulation mixture source (known as a pre-mix, ready-mix, concentrate, or formulated product).

In an embodiment, independent of other embodiments, a compound according to the present invention is applied as a combination. Accordingly, the present invention also provides a composition comprising a a compound according the invention as herein described and one or more other biological active agents, and optionally one or more customary formulation auxiliaries; which may be in the form of a tank-mix or pre-mix composition.

The compounds of formula (I) are particularly useful for controlling and preventing helminth and nematode endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, compounds of invention are especially useful for the control of helminths and nematodes. Examples for helminths are members of the class Trematoda, commonly known as flukes or flatworms, especially members of the genera *Fasciola, Fascioloides, Paramphistomu, Dicrocoelium, Eurytrema, Ophisthorchis, Fasciolopsis, Echinostoma* and *Paragonimus*. Nematodes which can be controlled by the formula (I) compounds include the genera *Haemonchus, Ostertagia, Cooperia, Oesphagastomu, Nematodirus, Dictyocaulus, Trichuris, Dirofilaria, Ancyclostoma, Ascaria* and the like.

For oral administration to warm-blooded animals, the compounds of the invention may be formulated as animal feeds, animal feed premixes, animal feed concentrates, pills, solutions, pastes, suspensions, drenches, gels, tablets, boluses and capsules. In addition, the compounds of the invention may be administered to the animals in their drinking water. For oral administration, the dosage form chosen should provide the animal with about 0.01 mg/kg to 100 g/kg of animal body weight per day of the compound of the invention.

Alternatively, the compounds of the invention may be administered to animals parenterally, for example, by intraluminal, intramuscular, intravenous or subcutaneous injection. The compounds of the invention may be dispersed or dissolved in a physiologically acceptable carrier for subcutaneous injection. Alternatively, the compounds of the invention may be formulated into an implant for subcutaneous administration. In addition the compounds of the invention may be transdermally administered to animals. For parenteral administration, the dosage form chosen should provide the animal with about 0.01 mg/kg to 100 mg/kg of animal body weight per day of the compound of the invention.

The compounds of the invention may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the compound of the invention. In addition, the compounds of the invention may be formulated as ear tags for animals, particularly quadrupeds such as cattle and sheep.

In an embodiment, independent of any other embodiments, a compound of formula (I) is a anti-helminth compound.

In an embodiment, independent of any other embodiments, a compound of formula (I) is a pesticidal compound, preferably a nematicidal compound.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples serve to illustrate the invention. They do not limit the invention. Temperatures are given in degrees Celsius; mixing ratios of solvents are given in parts by volume.

EXAMPLES

Preparation Example 1

3-Trifluoromethyl-pyridine-2-carboxylic acid [2-(2-fluoro-4-trifluoromethyl-phenyl)-ethyl]-amide (Compound A.001)

Step 1:
2-(2-fluoro-4-trifluoromethyl-phenyl)-ethylamine

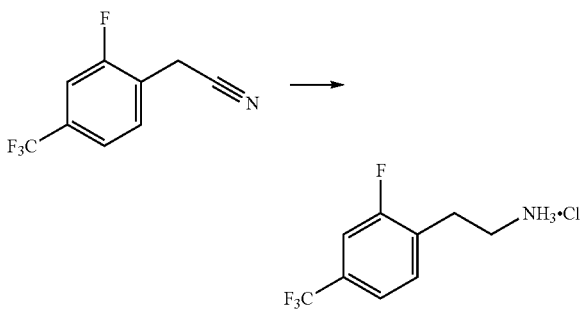

To palladium on carbon (10% wet; 262 mg, 2.46 mmol) under argon was added a solution of 2-fluoro-4-trifluoromethyl-phenyl)-acetonitrile (prepared according to the method reported by F. Stazi et al, Synthesis 2010, 19, 3332-3338; 10 g, 49.2 mmol) in ethanol (150 ml) and aqueous hydrochloric acid (9.85 ml). The reactor was sealed and the reaction mixture was stirred under 6 bar of hydrogen at ambient temperature for 14 hours. Then the reaction mixture was filtered over celite. After washing with ethanol and dichloromethane, the resulting filtrate was concentrated in vacuo. The residue was taken-up in diethyl ether and the resulting mixture was stirred for 30 min, then filtrated. The solid was washed with diethyl ether and dried in vacuo to afford 2-(2-fluoro-4-trifluoromethyl-phenyl)-ethylamine hydrochloride as a white powder.

$^1$H NMR (DMSO, 400 MHz) δ 2.95-3.15 (4H, m); 7.55-7.65 (2H, m); 7.68 (1H, d, J=10); 7.95-8.15 (3H, br s).

Step 2: 3-Trifluoromethyl-pyridine-2-carboxylic acid [2-(2-fluoro-4-trifluoromethyl-phenyl)-ethyl]-amide (Compound A.001)

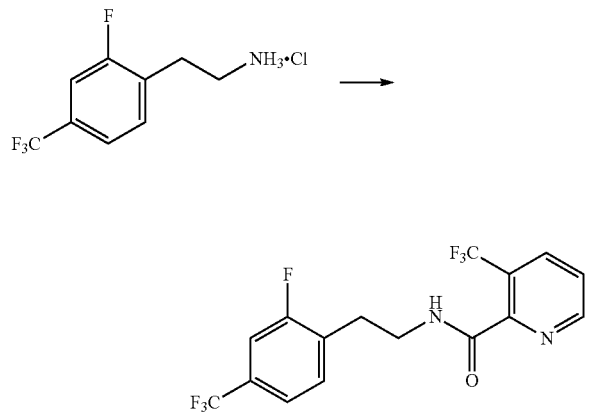

To a suspension of 3-trifluoromethyl-pyridine-2-carboxylic acid (4.20 g, 22.0 mmol) in toluene (22 ml) was added sequentially thionyl chloride (4.8 ml, 66 mmol) and DMF (two drops). The reaction mixture was heated at 110° C. for 2 h. After the gas evolution ceased, the reaction mixture was concentrated in vacuo to give 3-trifluoromethyl-pyridine-2-carbonyl chloride (4.65 g, 22. mmol) as a brown liquid which was directly used in the preparation of 3-trifluoromethyl-pyridine-2-carboxylic acid [2-(2-fluoro-4-trifluoromethyl-phenyl)-ethyl]-amide described below.

To a solution of 2-(2-fluoro-4-trifluoromethyl-phenyl)-ethylamine hydrochloride (5.00 g, 20.5 mmol) and triethylamine (8.7 ml, 62 mmol) in 41 ml of dichloromethane at 0° C. was added slowly 2-trifluoromethyl-nicotinoyl chloride (4.52 g, 21.5 mmol). The reaction mixture was stirred at 0° C. for 30 min. Then water was added, the phases were separated and the water phase was extracted three times with dichloromethane. The organic phases were combined, dried over anhydrous sodium sulfate, filtered and concentrated. The crude material obtained was purified by Combiflash® chromatography using dichloromethane as the eluent to afford 3-trifluoromethyl-pyridine-2-carboxylic acid [2-(2-fluoro-4-trifluoromethyl-phenyl)-ethyl]-amide as a beige powder.

$^1$H NMR (CDCl$_3$, 400 MHz) δ 3.00-3.10 (2H, m); 3.70-3.80 (2H, m); 5.75-5.90 (1H, br s); 7.30 (1H, d, J=10); 7.35-7.45 (2H, m); 7.50-7.60 (1H, m); 7.82 (1H, d); 8.20-8.30 (1H, m).

Preparation Example 2

3-Trifluoromethyl-pyridine-2-carboxylic acid [2-(4-chloro-2-fluoro-phenyl)-ethyl]-amide (Compound A.002)

Step 1: (4-Chloro-2-fluoro-phenyl)-acetonitrile

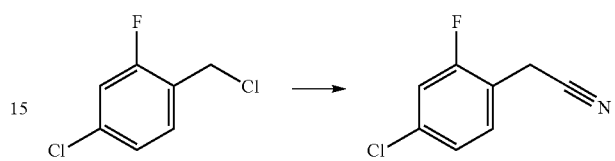

To a solution of 4-chloro-1-chloromethyl-2-fluoro-benzene (3.00 g, 16.8 mmol) in ethanol (17 ml) was added at ambient temperature a solution of sodium cyanide (0.90 g, 18.4 mmol) in water (5.0 ml). The reaction mixture was refluxed for 2 h and left at room temperature for 14 h. Ethanol was evaporated and the residue was diluted with water and extracted three times with ethyl acetate. The organic layers were combined, dried over sodium sulfate, filtered and concentrated under reduced pressure to give (4-chloro-2-fluoro-phenyl)-acetonitrile as a yellow oil which was used in the next step without further purification.

$^1$H NMR (CDCl$_3$, 400 MHz) δ 3.74 (2H, s); 7.15 (1H, dd, J=10 & 1); 7.20 (1H, dd, J=9 & 1); 7.40 (1H, dd, J=10 & 9).

Step 2: 2-(4-chloro-4-fluoro-phenyl)-ethylamine hydrochloride

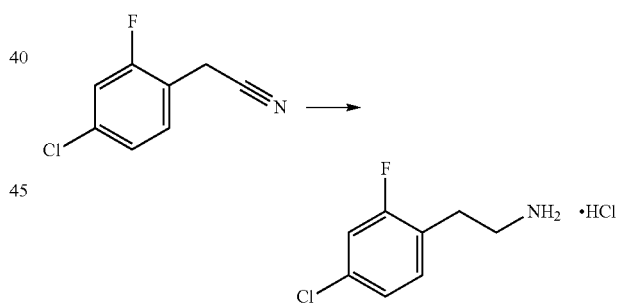

A solution of (4-chloro-2-fluoro-phenyl)-acetonitrile (1.80 g, 10.6 mmol) in dry tetrahydrofuran (21 ml) at 0° C. under argon was treated dropwise with borane tetrahydrofuran complex in THF (1 M, 31.8 ml, 32 mmol) and the reaction mixture was stirred at ambient temperature for 14 h. The reaction mixture was then cooled to 0° C. and methanol (12 ml) was added dropwise. The resulting mixture was stirred at ambient temperature for 1 h and then concentrated in vacuo to give 2.42 g of yellow oil. The oil was taken-up with 30 ml of HCl (1.25 M in methanol) and stirred for 2 h. The solvent was removed. The residue was triturated in diethyl ether and the product was isolated by filtration to give 2-(4-chloro-4-fluoro-phenyl)-ethylamine hydrochloride as a white powder.

$^1$H NMR (CDCl$_3$, 400 MHz) δ 2.75 (2H, t, J=8); 2.96 (2H, t, J=8); 7.00-7.10 (2H, m); 7.15 (1H, t, J=8).

Step 3: 3-Trifluoromethyl-pyridine-2-carboxylic acid [2-(4-chloro-2-fluoro-phenyl)-ethyl]-amide (Compound A.002)

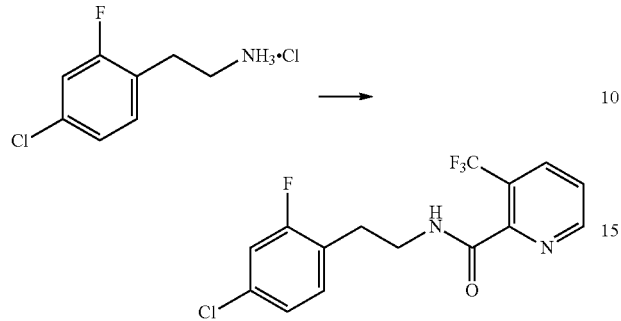

To a solution of 2-(4-chloro-2-fluoro-phenyl)-ethanamine hydrochloride (200 mg, 0.95 mmol) and triethylamine (0.33 ml, 2.38 mmol) in dichloromethane (4 ml) at ambient temperature was added 3-trifluoromethyl-pyridine-2-carboxylic acid (191 mg, 1.00 mmol) followed by 1-hydroxy-benzotriazole (257 mg, 1.90 mmol) and N-ethyl-N'-(3-dimethylaminopropyl)carbodiimide. The reaction mixture was stirred at ambient temperature for 14 h. The solvent was then removed under reduced pressure and the residue obtained was purified by Combiflash® chromatography using acetate/cyclohexane as the eluent to afford 3-trifluoromethyl-pyridine-2-carboxylic acid [2-(4-chloro-2-fluoro-phenyl)-ethyl]-amide as a white powder.

$^1$H NMR (CDCl$_3$, 400 MHz) δ 3.08 (2H, t, J=5); 3.75 (2H, q, J=5); 7.25-7.45 (3H, m); 7.58 (1H, dd, J=3 & 9); 7.75-7.85 (1H, br s); 8.18 (1H, d, J=9); 8.70 (1H, d, J=3).

Preparation Example 3

N-[2-(2,4-dichlorophenyl)-2,2-difluoro-ethyl]-3-methyl-pyridine-2-carboxamide (Compound A.009)

Step 1: 1-(2-bromo-1,1-difluoro-ethyl)-2,4-dichloro-benzene

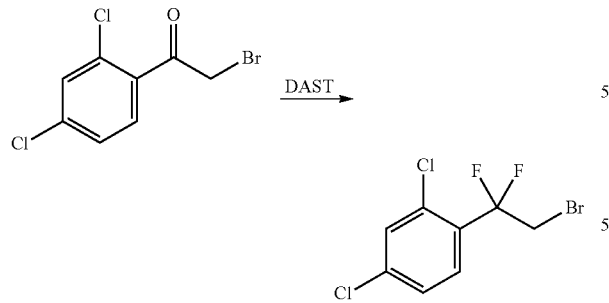

A solution of 2-bromo-1-(2,4-dichlorophenyl)ethanone (5 g, 18.7 mmol) in diethylaminosulfur trifluoride (DAST; 3.43 ml, 28.0 mmol) was stirred at room temperature for one week. The yellow solution was diluted with dichloromethane (10 ml), sodium carbonate solution 10% (5 ml) was carefully added dropwise, with exothermic gas evolution. Phases were separated and the aqueous layer was extracted with dichloromethane. The organic phases were washed with water and brine, dried over sodium sulfate, filtered and concentrated to give of the crude product, which was chromatographed on silica gel with ethyl acetate/cyclohexane 20:1 to yield 1-(2-bromo-1,1-difluoro-ethyl)-2,4-dichlorobenzene as a yellow oil.

$^1$H NMR (CDCl3, 400 MHz) δ 4.00 (2H, t, J=14); 7.35 (1H, dd, 8 & 2); 7.48 (1H, s); 7.59 (1H, d, J=8).

Step 2: 1-(2-azido-1,1-difluoro-ethyl)-2,4-dichloro-benzene

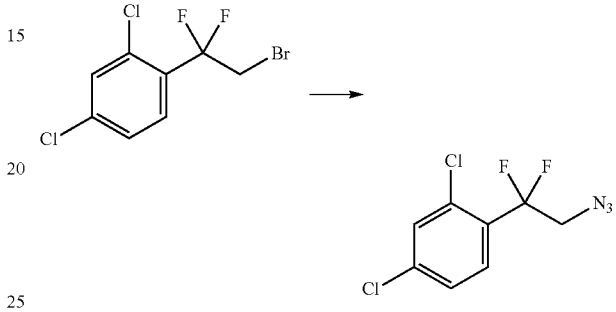

To a solution of sodium azide (374 mg, 5.69 mmol) in dimethyl sulfoxide (11 ml) was added at room temperature 1-(2-bromo-1,1-difluoro-ethyl)-2,4-dichloro-benzene (1.5 g, 5.17 mmol). The reaction mixture was heated to 110° C. and became rapidly a black solution and then light brown. The reaction mixture was stirred at 110° C. overnight. Then it was cooled to 10° C. and water was added. The mixture was extracted with diethyl ether. The organic phases were washed with brine, dried over sodium sulfate, filtered and concentrated to give 1-(2-azido-1,1-difluoro-ethyl)-2,4-dichloro-benzene of crude product which was used without further purification.

$^1$H NMR (CDCl3, 400 MHz) δ 3.94 (2H, t, J=13); 7.36 (1H, dd, J=8 & 2); 7.49 (1H, s); 7.59 (1H, d, J=8).

Step 3: 2-(2,4-dichlorophenyl)-2,2-difluoro-ethanamine

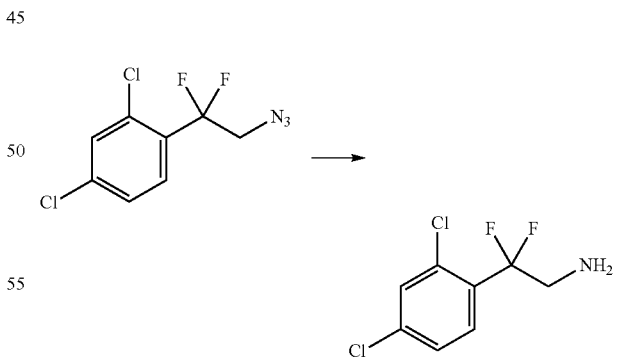

1-(2-azido-1,1-difluoro-ethyl)-2,4-dichloro-benzene (1.12 g, 4.44 mmol) was dissolved in ethyl acetate (45 ml) and the solution was flushed with argon. Palladium on activated carbon (10%; 0.111 g) was added and the reaction mixture was stirred at room temperature under hydrogen atmosphere overnight. The reaction mixture was filtered over celite and the filtrate was concentrated to give 2-(2,4-dichlorophenyl)-2,2-difluoro-ethanamine as a yellow liquid.

$^1$H NMR (CDCl3, 400 MHz) δ 3.37 (2H, t, J=14); 7.33 (1H, dd, J=8 & 2); 7.47 (1H, s); 7.55 (1H, d, J=12).

Step 4: N-[2-(2,4-dichlorophenyl)-2,2-difluoroethyl]-3-methyl-pyridine-2-carboxamide (Compound A.009)

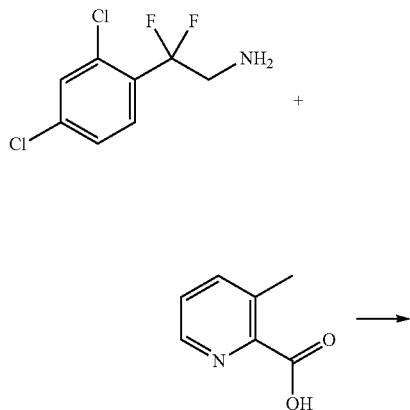

+

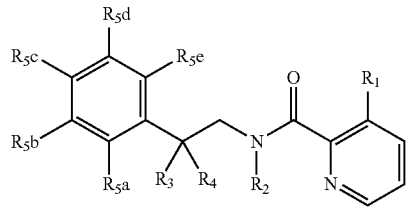

→

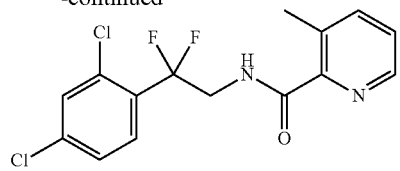

To a solution of 2-(2,4-dichlorophenyl)-2,2-difluoroethanamine (100 mg, 0.442 mmol) in dichloromethane (2 ml) was added, at room temperature, triethylamine (123 μl, 0.885 mmol), 3-methylpyridine-2-carboxylic acid (60.7 mg, 0.442 mmol), 1-hydroxybenzotriazole (135 mg, 0.885 mmol) and finally N-(3-dimethylaminopropyl)-N'-ethylcarbodiimide hydrochloride (170 mg, 0.885 mmol). The mixture was stirred at room temperature overnight. The reaction mixture was diluted with ethyl acetate and extracted with water and brine, dried over sodium sulfate, filtered and concentrated to give 150 mg of crude product, which was chromatographed on silica gel with ethyl acetate/cyclohexane 3:1 to yield N-[2-(2,4-dichlorophenyl)-2,2-difluoroethyl]-3-methyl-pyridine-2-carboxamide as a white solid.

$^1$H NMR (CDCl3, 400 MHz) δ 2.67 (3H, s); 4.28 (2H, td, J=16 & 8); 7.31 (2H, m); 7.49 (1H, s); 7.57 (2H, t, J=8); 8.39 (1H, d, J=4); 8.50 (1H, bs).

According to the methods described above, the compounds in Table A were prepared.

TABLE A

Compounds of formula (Id).

(Id)

| Comp. No. | R1 | R2 | R3 | R4 | R5a | R5b | R5c | R5d | R5e | Phys. data |
|---|---|---|---|---|---|---|---|---|---|---|
| A.001 | CF3 | H | H | H | H | H | CF3 | H | F | LCMS: 1.01 min, 381 (M + 1) Mp: 95° C. |
| A.002 | CF3 | H | H | H | H | H | Cl | H | F | LCMS: 0.98 min, 347 (M + 1), Mp: 69° C. |
| A.003 | CF3 | H | H | H | H | H | Br | H | F | LCMS: 1.01 min, 391 (M + 1), Mp: 77° C. |
| A.004 | Cl | H | H | H | H | H | Br | H | F | LCMS: 0.91 min, 357 (M + 1), Mp: 79° C. |
| A.005 | CF3 | H | H | H | H | H | F | H | F | LCMS: 0.93 min, 331 (M + 1), Mp: 78° C. |
| A.006 | Cl | H | H | H | H | H | F | H | F | LCMS: 0.89 min, 297 (M + 1) Mp: 87° C. |
| A.007 | CH3 | H | F | | H | H | Cl | H | Cl | Mp: 134-6° C. |
| A.008 | CH3 | H | F | F | H | H | H | H | H | LCMS: 0.92 min, 277 (M + 1) |

TABLE A-continued

Compounds of formula (Id).

(Id)

| Comp. No. | R$_1$ | R$_2$ | R$_3$ | R$_4$ | R5a | R5b | R5c | R5d | R5e | Phys. data |
|---|---|---|---|---|---|---|---|---|---|---|
| A.009 | CH3 | H | F | F | H | H | Cl | H | Cl | Mp: 117-8° C. |
| A.010 | CH3 | H | F | F | H | H | Cl | H | H | LCMS: 1.80 min, 311 (M + 1) |
| A.011 | CF3 | H | H | H | F | H | F | H | F | Mp: 106-7° C. |
| A.012 | CF3 | H | H | H | F | H | CF3 | H | CF3 | Mp: 97-8° C. |
| A.013 | CF3 | H | H | H | F | F | H | H | H | Mp: 112-3° C. |
| A.014 | CF3 | H | H | H | F | Cl | H | H | H | Mp: 95-6° C. |
| A.016 | CF3 | H | H | H | Cl | H | F | H | H | Mp: 92-3° C. |
| A.017 | CF3 | H | H | H | Cl | H | OCH3 | H | H | Mp: 87-8° C. |
| A.018 | CF3 | H | H | H | F | H | H | H | Cl | Mp: 114-5° C. |
| A.019 | CF3 | H | H | H | H | F | F | F | H | Mp: 127-8° C. |
| A.020 | Cl | H | H | H | F | H | F | H | F | Mp: 139-40° C. |
| A.021 | Cl | H | H | H | F | H | CF3 | H | CF3 | Mp: 102-3° C. |
| A.022 | Cl | H | H | H | F | F | H | H | H | Mp: 74-5° C. |
| A.023 | Cl | H | H | H | F | Cl | H | H | H | Mp: 95-6° C. |
| A.024 | Cl | H | H | H | F | H | H | H | Cl | Mp: 97-8° C. |
| A.025 | Cl | H | H | H | F | H | H | H | F | Mp: 116-7° C. |
| A.026 | Cl | H | H | H | Cl | H | F | H | H | Mp: 90-1° C. |
| A.027 | Cl | H | H | H | Cl | H | OCH3 | H | H | Mp: 104-5° C. |
| A.028 | Cl | H | H | H | H | F | F | F | H | Mp: 121-2° C. |
| A.029 | CF3 | H | H | H | Cl | H | Cl | H | H | Mp: 76-7° C. |
| A.030 | CF3 | H | H | H | Br | H | H | H | H | Mp: 90-1° C. |
| A.031 | CF3 | H | H | H | CH3 | H | H | H | H | LCMS: 0.98 min, 309 (M + 1) |
| A.032 | CF3 | H | H | H | OCH3 | H | H | H | H | Mp: 88-9° C. |
| A.033 | CF3 | H | H | H | H | H | CF3 | H | H | Mp: 99-100° C. |
| A.034 | CF3 | H | H | H | H | H | F | H | H | Mp: 68-9° C. |
| A.036 | Cl | H | H | H | F | H | CF3 | H | H | Mp: 108-9° C. |
| A.037 | Cl | H | H | H | Br | H | H | H | H | Mp: 141-2° C. |
| A.038 | Cl | H | H | H | CH3 | H | H | H | H | Mp: 74-5° C. |
| A.039 | Cl | H | H | H | OCH3 | H | H | H | H | LCMS: 0.90 min, 291/3 (M + 1) |
| A.040 | Cl | H | H | H | H | H | CF3 | H | H | Mp: 126-7° C. |
| A.041 | Cl | H | H | H | H | H | F | H | H | LCMS: 0.87 min, 279/81 (M + 1) |

LC-MS method: ZCQ12
ZQ Mass Spectrometer from Waters (Single quadrupole mass spectrometer)
Instrument Parameter:
Ionization method: Electrospray
Polarity: positive and negative ions
Capillary: 3.00 kV
Cone: 30 V
Extractor: 2.00 V
Source Temperature: 150° C.,
Desolvation Temperature: 350C
Cone Gas Flow: 50 L/Hr
Desolvation Gas Flow: 400 L/Hr
Mass range: 100 to 900 Da
Acquity UPLC from Waters:
Binary pump, heated column compartment and diode-array detector.
Solvent degasser, binary pump, heated column compartment and diode-array detector.

Column: Waters UPLC HSS T3, 1.8µ 1.8 1, 30×2.1 mm, Temp: 60° C.
DAD Wavelength range (nm): 210 to 500
Solvent Gradient:
A=H$_2$O+5% MeOH+0.05% HCOOH
B=Acetonitril+0.05% HCOOH

| Time | A % | B % | Flow (ml/min) |
|---|---|---|---|
| 0.00 | 90 | 10 | 0.85 |
| 1.20 | 0 | 100.0 | 0.85 |
| 1.50 | 0 | 100.0 | 0.85 |

BIOLOGICAL EXAMPLES

*Meloidowne* Spp. (Root-Knot Nematode) Contact Activity, Preventive. (1 ml)

Filter papers (9 cm×4.5 cm) with a small pocket were placed into plastic pouches (12 cm×6 cm). One cucumber cv. Toshka seed was placed in the centre of the filter paper pocket of all the pouches needed for a test. The cucumber seeds in the pouches were treated with test solutions at 200 ppm by pipetting the solution directly over the cucumber seed in the filter paper pocket in the pouch. Prior to application, the compound solution was prepared at twice the concentration required and the egg suspension is prepared with FORL nutrient solution with 3000 eggs/0.5 ml. After applying all the treatments, 3000 eggs (in 0.5 ml of FORL nutrient solution) were pipetted into the pouches. The pouches were incubated in a moist chamber for twelve days and watered regularly to maintain good filter paper moisture essential for the growing cucumber root system. After this period, the filter paper containing the germinated cucumber seedling was removed from the plastic pouch to assess the number of galls caused by *Meloidogyne* spp. per root system.

The following compounds showed a greater than 80% reduction of galling compared to the untreated control: A.001, A.002, A.003, A.005, A.008, A.016, A.029, A.034 and A.041.

*Meloidowne* Spp. (Root-Knot Nematode) Contact Activity, Preventive.

Cucumber cv. Toshka seeds were sown directly into pots filled with a sandy substrate. Six days later pots were each treated with 5 ml of a WP10 suspension of the test compound at 20 ppm. Hereafter pots were inoculated with 3000 eggs of *M. incognita*. The trial was harvested fourteen days after trial application and inoculation. Root galling was assessed according to Zeck's gall index (Zeck, 1971).

The following compounds showed a greater than 80% reduction of galling compared to the untreated control: A.001, A.002, A.003, A.004, A.005, A.006, A.009, A.011, A.013, A.016, A.019, A.020, A.022, A.023, A.025, A.026, A.028, A.029, A.030, A.031, A.033, A.034 and A.041.

*Heterodera schachtii* (Sugar Beet Cyst Nematode), Contact Activity

The tested application rate of each compound was 200 ppm. All solutions were brought to a concentration of 400 ppm, respectively, as they were subsequently diluted by adding the equivalent amount of water containing juvenile nematodes. After preparation of the suspensions, 1 ml of each suspension and concentration was transferred to 16-well assay plates with a total of three replicates per treatment. Approximately 500 juveniles of *Heterodera schachtii* were added in 1 ml of water to each well. Nematodes in water served as controls. The plates were placed in a dark box and stored at room temperature. Nematode paralysis was determined after 24 hours incubation at 25° C. in darkness. Nematodes that showed no movement were considered immotile.

The following compounds showed a greater than 75% nematode immobilization compared to the untreated control: A.001, A.002, A.003, A.004, A.011, A.016, A.029 and A.033.

*Heterodera schachtii* (Sugar Beet Cyst Nematode), Contact Activity, Preventive

Coated sugar beat cv. Impulse seeds were planted in 45 ml pots filled with field soil. Seven days after sowing pots were infested with 500 J2 of *Heterodera schachtii* within a 2 ml suspension in two holes to the left and right of the seedling. Assessment of nematode numbers per g of root occurred 10 days after inoculation. The upper plant part was cut off and the roots were washed free of soil debris. Nematodes within the roots were stained with acid fuchsin stain solution. Nematodes within the roots were quantified under a dissecting scope at 40×.

Seed treatment rate: 0.6 mg AI/seed

The following compounds showed a greater than 80% reduction of nematode population compared to the untreated control: A.001 and A.002.

The invention claimed is:

1. A method of protecting crops of useful plants against damages caused by nematode pests, which comprises treating the plants or the locus thereof with a compound of the formula (I)

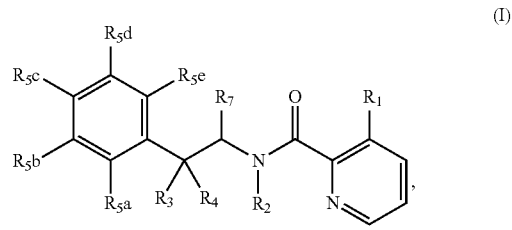

wherein

R1 represents halogen, methyl or trifluoromethyl;

R2 represents hydrogen;

R3 and R4 independently of each other represent hydrogen or fluorine;

R5a represents hydrogen, bromo, cyano, difluoromethyl, trifluoromethyl, difluoromethoxy or trifluoromethoxy;

R5b represents hydrogen, fluoro, chloro, bromo, cyano, difluoromethyl, trifluoromethyl, difluoromethoxy or trifluoromethoxy;

R5c represents hydrogen, fluoro, bromo, cyano, difluoromethyl, trifluoromethyl, difluoromethoxy or trifluoromethoxy;

R5d represents hydrogen, fluoro, chloro, bromo, cyano, difluoromethyl, trifluoromethyl, difluoromethoxy or trifluoromethoxy;

R5e represents hydrogen, fluoro, chloro, bromo, cyano, difluoromethyl, trifluoromethyl, difluoromethoxy or trifluoromethoxy; and R7 represents hydrogen;

or an agronomically acceptable salt, enantiomer, diastereomer, tautomer or N-oxides thereof.

2. A method according to claim 1 wherein R3 and R4 each represent fluorine.

3. A method according to claim 1 wherein R3 represents hydrogen and R4 represents fluorine.

4. A method according to claim 1 wherein R3 and R4 each represent hydrogen.

5. A compound of formula (I)

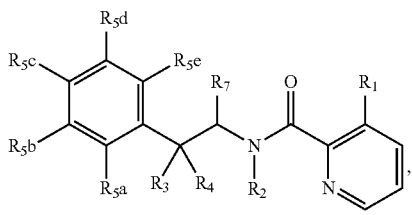

wherein
R1 represents halogen, methyl or trifluoromethyl;
R2 represents hydrogen;
R3 and R4 independently of each other represent hydrogen or fluorine;
R5a, R5b, R5d each represent hydrogen;
R5c represents fluoro, chloro, bromo, cyano, difluoromethyl, trifluoromethyl, difluoromethoxy or trifluoromethoxy;
R5e represents fluoro; and
R7 is hydrogen.

6. A compound according to formula (I) as defined in claim 1, as well as agronomically acceptable salts, enantiomers, diastereomers, tautomers and N-oxides of these compounds, provided that the compound of formula (I) is not:

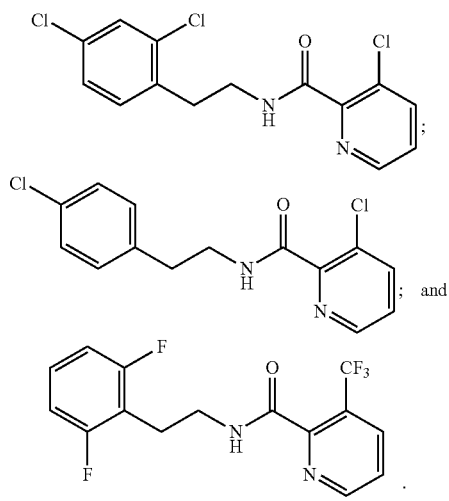

7. A compound of formula (I)

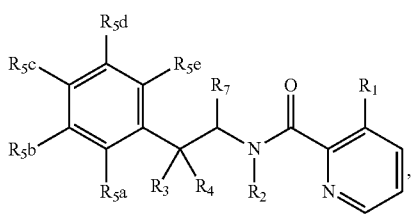

wherein
R1 represents halogen, cyano, C1-C2-alkyl, C1-C2-haloalkyl, C1-C2-alkoxy, C1-C2-haloalkoxy or C1-C2-haloalkylthio;
R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl, C3-C6-cycloalkoxy or benzyl;
R3 and R4 independently of each other represent hydrogen and fluorine;
R5a represents hydrogen, fluoro, bromo, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;
R5b and R5d independently of each other represent hydrogen, halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;
R5c represents halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;
R5e represents fluoro;
each R6 independently of each other represents halogen, C1-C4-alkyl or C1-C4-haloalkyl; and
R7 represents hydrogen or methyl;
or an agronomically acceptable salt, enantiomer, diastereomer, tautomer or N-oxide thereof.

8. A compound of formula (I)

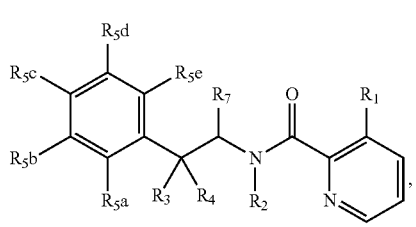

wherein
R1 represents halogen, cyano, C1-C2-alkyl, C1-C2-haloalkyl, C1-C2-alkoxy, C1-C2-haloalkoxy or C1-C2-haloalkylthio;
R2 represents hydrogen, C1-C4-alkyl, C1-C4-alkoxycarbonyl, C1-C4-alkoxy, cyanomethyl, C2-C4-alkenyl, C2-C4-alkynyl, C3-C6-cycloalkylcarbonyl, C3-C6-cycloalkoxyor benzyl;
R3 and R4 independently of each other represent hydrogen and fluorine;
R5a represents hydrogen, fluoro, bromo, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5b and R5d independently of each other represent hydrogen, halogen, cyano, C1-C4-alkyl, C1-C4-haloalkyl, C1-C4-alkoxy, $C_1$-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5c represents hydrogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C3-C6-cycloalkyl, C2-C6-alkenyl or C2-C6 haloalkynyl, wherein cycloalkyl is optionally substituted by one or more substituents R6 and alkenyl is substituted by one or more R6;

R5e represents chloro;

each R6 independently of each other represents halogen, C1-C4-alkyl or C1-C4-haloalkyl; and R7 represents hydrogen or methyl;

or an agronomically acceptable salt, enantiomer, diastereomer, tautomer or N-oxide thereof.

9. A pesticidal composition, which, in addition to comprising formulation adjuvants, comprises a nematicidal effective amount of a compound of the formula I according to claim 8.

10. A composition according to claim 9, which further comprises one or more insecticidally, acaricidally, nematicidally and/or fungicidally active agents.

11. A method of protecting crops of useful plants against damages caused by nematode pests, which comprises treating the plants or the locus thereof with a composition according to claim 9.

12. A method of protecting plant propagation material against damages caused by nematode pests, which comprises treating the material with a composition according to claim 9.

13. A process for the preparation of compounds of formula (Ib)

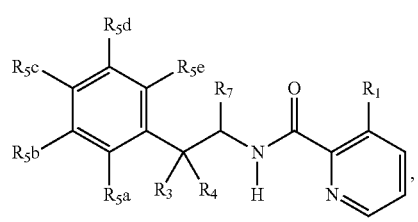

(Ib)

wherein R1, R3, R4, R5a, R5b, R5c, R5d, R5e and R7 are as defined for compound of formula (I) in claim 1, comprising reacting a compound of formula (II), wherein R3, R4, R5a, R5b, R5c, R5d, R5e and R7 are as defined for compounds of formula (I) in claim 1, with acylating agents of formula (III), wherein Xb is halogen, hydroxy or $C_{1-6}$ alkoxy and R1 is as defined for compounds of formula (I) in claim 1, in the presence of a base to yield a compound of formula (Ib)

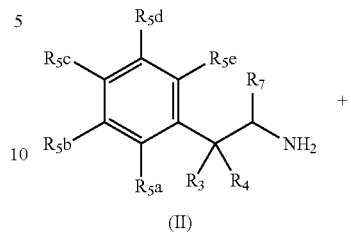

(II)

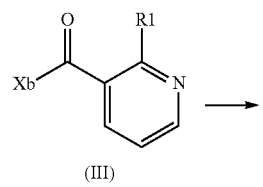

(III)

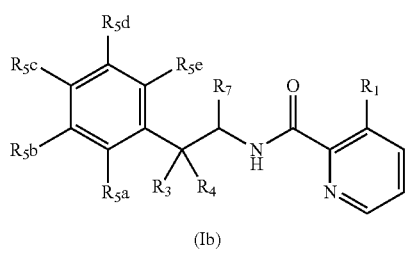

(Ib)

14. A process for the preparation of compounds of formula (I) defined in claim 1, wherein R2 is not hydrogen and R5e is fluorine, comprising reacting a compound of formula (Ib),

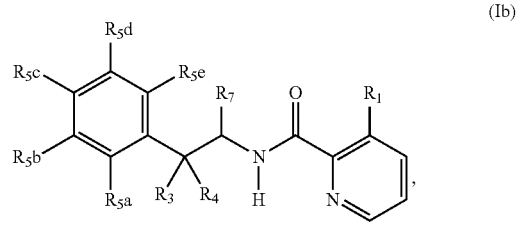

(Ib)

wherein R1, R3, R4, R5a, R5b, R5c, R5d, R5e and R7 are as defined for compound of formula (I) in claim 1, with a reagent of formula (VI), wherein R2 is as defined in claim 1 but is not hydrogen and Xc is a leaving group

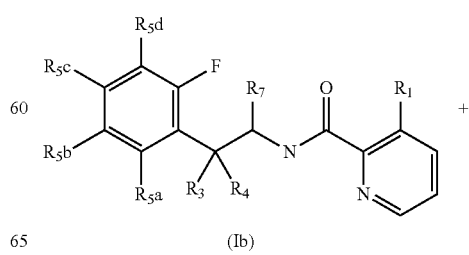

(Ib)

-continued

Xc—R₂ ⟶

(VI)

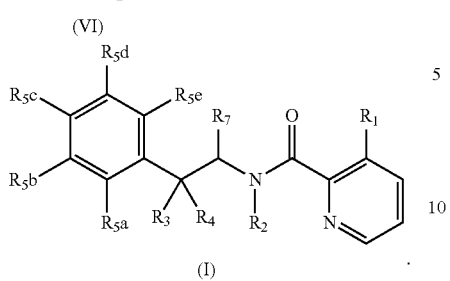

(I)

15. The method of claim 1, wherein R5a represents hydrogen, bromo, cyano, difluoromethyl, trifluoromethyl, difluoromethoxy or trifluoromethoxy;

R5b represents hydrogen, fluoro, chloro, bromo, cyano, difluoromethyl, trifluoromethyl, difluoromethoxy or trifluoromethoxy;

R5c represents hydrogen, fluoro, bromo, cyano, difluoromethyl, trifluoromethyl, difluoromethoxy or trifluoromethoxy;

R5d represents hydrogen, fluoro, chloro, bromo, cyano, difluoromethyl, trifluoromethyl, difluoromethoxy or trifluoromethoxy; and R5e represents hydrogen, fluoro, bromo, cyano, difluoromethyl, trifluoromethyl, difluoromethoxy or trifluoromethoxy.

16. The method of claim 15, wherein R5c represents hydrogen, fluoro, cyano, difluoromethyl, trifluoromethyl, difluoromethoxy or trifluoromethoxy.

17. The method of claim 1, wherein R3 represents fluorine.

18. The method of claim 1, wherein R1 represents methyl.

19. The method of claim 1, wherein the nematode pests are *Heterodera schachtii* and *Meloidogyne* Spp.

* * * * *